United States Patent [19]

Dewhirst

[11] Patent Number: 4,786,668

[45] Date of Patent: Nov. 22, 1988

[54] RESIN MATERIALS

[75] Inventor: Kenneth C. Dewhirst, Houston, Tex.

[73] Assignee: Shell Oil Company, Houston, Tex.

[21] Appl. No.: 871,951

[22] Filed: Jun. 9, 1986

[51] Int. Cl.$^4$ .................... C08G 59/00; C08G 59/24
[52] U.S. Cl. .................... 523/445; 523/466; 523/468; 525/438; 528/97; 528/98; 528/99; 528/104
[58] Field of Search ............ 528/97, 98, 99, 104, 528/27; 523/445, 466, 468; 525/438

[56] References Cited

U.S. PATENT DOCUMENTS

| | | | |
|---|---|---|---|
| 3,306,872 | 2/1967 | Maycock et al. | 260/32.8 |
| 3,410,825 | 11/1968 | Coover et al. | 528/97 |
| 3,419,624 | 12/1968 | Cotter et al. | 528/97 X |
| 3,546,165 | 12/1970 | Morgan | 260/47 |
| 3,635,843 | 1/1972 | Parry et al. | 528/97 |
| 3,637,590 | 1/1972 | Maycock et al. | 260/47 EP |
| 3,725,341 | 4/1973 | Rogers et al. | 528/97 X |
| 3,795,658 | 3/1974 | Thompson et al. | 528/97 |
| 3,821,162 | 6/1974 | Dexter | 260/45.8 N |
| 4,394,497 | 7/1983 | Nelson et al. | 528/97 X |
| 4,473,674 | 9/1984 | Stoakley et al. | 523/454 |
| 4,647,648 | 3/1987 | Silvis et al. | 528/102 |
| 4,672,102 | 9/1987 | Silvis et al. | 528/97 |

FOREIGN PATENT DOCUMENTS 2142579 9/1972 Fed. Rep. of Germany .

OTHER PUBLICATIONS

Kourtides et al., "Advanced Thermoset Resins for Fire-Resistant Composites", 11th Nat. SAMPE Technical Conference, pp. 551–563 (1979).
Fire-Resistant Composites", NASA Tech. Briefs, Spring 1983, p. 285.
J. F. McGrath, 29th National SAMPE Symposium, Apr. 3–5, 1984, pp. 447–458.

*Primary Examiner*—Earl Nielsen
*Attorney, Agent, or Firm*—Dean F. Vance

[57] ABSTRACT

The present invention relates to a new thermoplastic polymer composition having the processing characteristics of a thermosetting polymer along with an improved balance of properties including solvent resistance and improved modulus/glass transition temperature/toughness balance. These new polymer compositions are prepared by reacting certain diphenolic compounds with certain diepoxide compounds to form linear units which are lightly crosslinked through the resulting secondary hydroxyl groups. Also disclosed and claimed are processes for preparing such compositions, cured compositions and end-use applications.

59 Claims, 3 Drawing Sheets

RESIN PROPERTIES VS. BPFL CONTENT (1) DSC
(2) MINI-COMPACT TENSION
(3) ROOM TEMPERATURE, 24 HOURS
(4) PHENOL AND EPOXY

RESIN PROPERTIES VS. CROSS LINK DENSITY (3)

(1) DSC
(2) MINI-COMPACT TENSION
(3) CROSS LINKER = EPON® RESIN 1031

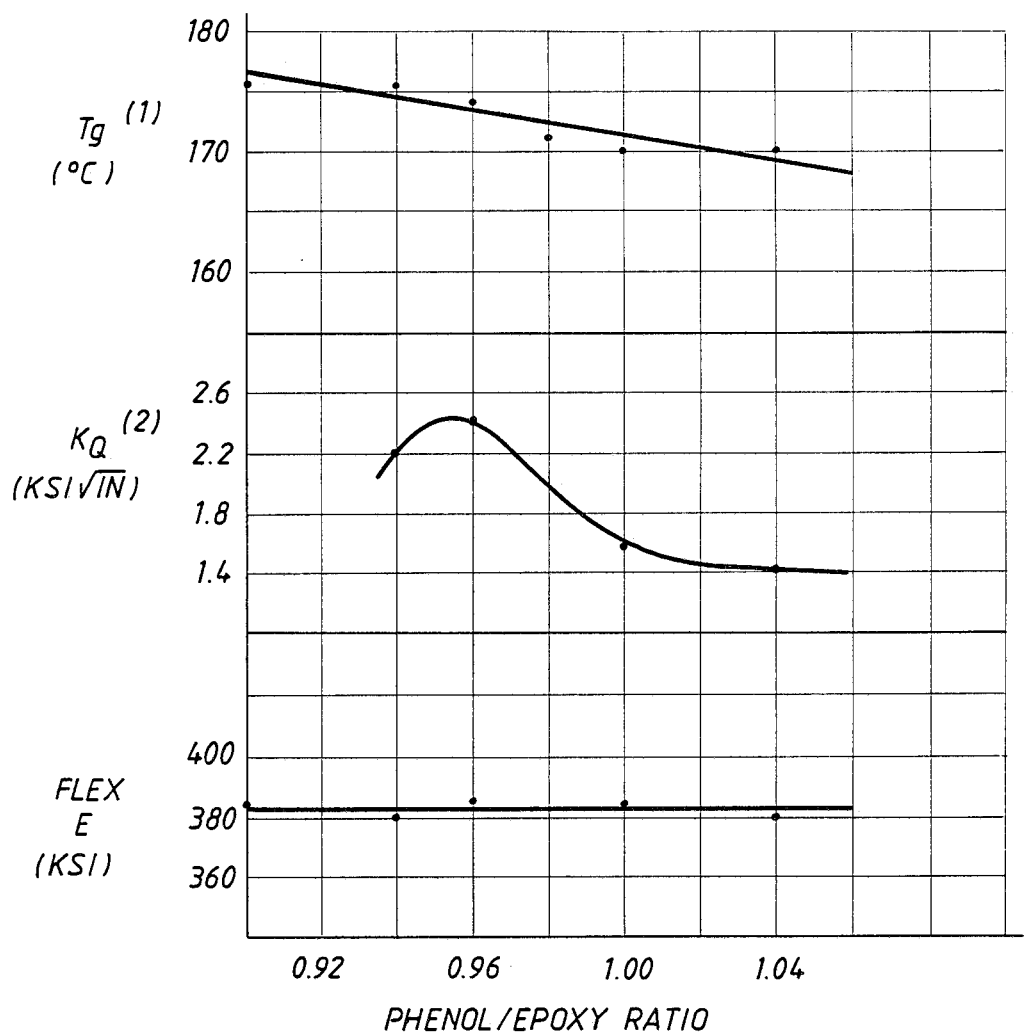

RESIN MATERIALS

FIELD OF THE INVENTION

The present invention relates to novel and unobvious thermoplastic compositions which may be fabricated into thermoset composite structures by typical thermosetting resin methods. In particular, the present invention relates to thermoplastic compositions having flexible portions and bulky stiff portions, prepared by reacting a polyepoxide with a polyphenol to form linear molecules and lightly crosslinking the resulting linear molecules.

BACKGROUND OF THE INVENTION

Epoxy compositions and their curing techniques are well known, and the patents issued on curable epoxy compositions number in the hundreds. It will be appreciated that each and every one of the known epoxy-curing systems exhibits advantages over other systems, and, as importantly, disadvantages over the same systems. There is, of course, a continuing need to develop better epoxy compositions.

There is, in particular, an increasing need in the aerospace and automotive sectors for high performance thermosetting compositions or matrices for fiber reinforced composites. Fiber reinforced composites are very desirable in aerospace applications because they can offer a combination of good stiffness, strength and are light weight. Increasingly, the aerospace manufacturers have demanded higher performance from the thermoset resins used in fiber reinforced composites. These higher performance thermoset resins are expected to possess these following characteristics:
 good mechanical properties at temperatures above about 90° C.
 good thermal oxidative stability
 good toughness properties, including good impact resistance
 good fatigue properties
 good chemical and solvent resistance
 good fire resistance
 high resistance to humidity, e.g., the "hot-wet" properties of the composite must remain high.

A further, and very important property of such systems is that the composite must have acceptable processing characteristics. For example, the current techniques for manufacturing aerospace components typically involves the use of prepregs and laminates, which are cured by applying heat and pressure in a vacuum bag/autoclave-type apparatus. Therefore, the most desirable thermosetting resin compositions should be processable on the standard equipment currently utilized in the aerospace industry.

A broad spectrum of thermosetting epoxy resin systems is currently being used by the aerospace industry, primarily as composite matrices and adhesives. As a class, epoxy resin systems are very versatile materials offering, as mentioned above, chemical resistance, high adhesive strength, good electric properties and are easy to use or process into composites. However, to improve their high temperature properties, such current epoxy resin systems must be highly crosslinked. This crosslinking, however, results in generally lower toughness.

There are currently various engineering thermoplastics (not thermosetting polymers) that offer excellent high temperature properties along with high toughness. One such example currently being investigated is the use of poly(ether-ether)ketone ("PEEK") as the matrix. However, there are processing problems with the use of PEEK and other similar engineering thermoplastic resins since such materials not only are difficult to process on thermoplastic apparatus (i.e., difficult to extrude), but also do not lend themselves to processing by the thermosetting techniques now currently in use by the aerospace industry.

What is needed is a resin system that only combines the good property advantages of such high performance engineering thermoplastics such as PEEK, but is also processable as a thermosetting resin matrix.

DESCRIPTION OF THE PRIOR ART

Thermoplastic polyethers having relatively high impact strength are disclosed and claimed in U.S. Pat. No. 3,637,590, while the process for preparing such polymers is claimed in U.S. Pat. No. 3,306,872. Even though such polymers, which are based on the reaction product of certain diepoxides with certain bisphenols, have improved impact strength, such polymers lack adequate high temperature properties and solvent resistance for high performance applications. Similar compositions having improved impact strength are also disclosed in Fed. Rep. of Germany OLS 2,142,579 where certain diepoxides are reacted with certain diphenols (e.g. 2,2-bis(4-hydroxynaphth-1-yl)propane) to produce polymers for eyeglasses.

Thermosetting resins having improved performance characteristics are disclosed in the article "Advanced Thermoset Resins for Fire-Resistant Composites", by Kourtides et al, 11th National SAMPE Technical Conference, pages 551–563 (1979). While the thermoset resins disclosed therein, such as the epoxy resins based on the diglycidyl ether of bisphenol A and the diglycidyl ether of bisphenol fluorenone, have improved high temperature properties, they also lack adequate toughness for truly high performance applications. See also Fire-Resistant Composites, NASA Tech Briefs, Spring 1983, p. 285.

Other epoxy systems such as those disclosed in U.S. Pat. No. 4,473,674, are touted for aerospace applications. The composites described in the '674 patent are based on multifunctional epoxies, such as tetraglycidyl-methylenedianiline cured with DDS. Such systems also have important deficiencies as discussed in the various examples which follow.

SUMMARY OF THE INVENTION

The present invention relates to a thermoplastic composition having the processing characteristics of a thermosetting polymer along with an improved balance of properties including solvent resistance and improved modulus/glass transition temperature/toughness balance. In particular the present invention relates to a thermoplastic composition comprising linear molecules having the repeating structures:

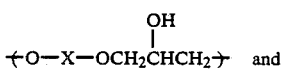

and

where:

(a) "X" represents a stiff segment comprising stiff units (SU) and optional flexible units (FU), which stiff units and flexible units are interconnected;

(b) "Y" represents a flexible segment comprising stiff units (SU') and optional flexible units (FU') which stiff units and flexible units are interconnected;

(c) said stiff units, SU and SU', are independently selected from the group consisting of substituted and non-substituted aromatic rings, cycloaliphatic rings and heterocyclic rings;

(d) said flexible units, FU and FU', are independently selected from the group consisting of

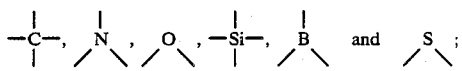

(e) the number of stiff segments in said molecules are "a", the number of flexible segments in said molecules are "b", and the ratio of
(a/a+b) is between zero and one;

(f) the number of stiff units and flexible units are selected such that the average number of total stiff units $$\left(\frac{a}{a+b} \cdot SU + \frac{b}{a+b} \cdot SU'\right)$$

divided by the average number of total flexible units $$\left(\frac{a}{a+b} \cdot FU + \frac{b}{a+b} \cdot FU'\right)$$

is greater than four;

(g) the ratio of the number of stiff units to flexible units in said stiff segment (SU/FU) is equal to or greater than the ratio of the number of stiff units to flexible units in said flexible segment (SU'/FU'); and (h) said composition having a glass transition temperature of at least about 150° C., a flex modulus of at least 350 KSI and a fracture toughness of at least 1000 psi $\sqrt{in}$.

In another embodiment, this invention relates to a process for preparing such thermoplastic polymers, said process comprising reacting:

(c) a first component selected from the group consisting of phenol compounds of the formula HO—X—OH or HO—Y—OH, where X and Y represent the stiff segment and flexible segment respectively, defined above; with (b) a second component, said second component being a diepoxide selected from the groups consisting of HO—Y—OH, then the diepoxide is chosen from the structure of formula III; and (c) a catalytic amount, not in excess of 0.1 mole per mole of said first component, of a basic condensation catalyst at a temperature of about 130° to about 230° C. for about 1 to about 24 hours and with a molar ratio of phenol compounds to diepoxides of about 0.90:1 to about 1.04:1 until the desired linear reaction product has been formed, and thereafter stopping the reaction.

In another embodiment, the first and second components specified for use in the above process may be premixed and sold or stored (with or without catalyst) for later reaction.

Also disclosed and claimed herein are lightly crosslinked compositions, compositions containing fibrous reinforcing materials, prepregs prepared from such reinforced compositions and articles prepared from such prepregs.

ADVANTAGES AND OBJECTS OF THE PRESENT INVENTION

One object of the present invention is to produce thermoplastic polymers having the processing characteristics of thermosetting polymers, while also having the high performance characteristics of premium thermoplastic polymers.

Another object of the present invention is to tailor make polymers for particular applications, i.e., to design polymers having the required balance of solvent resistance, thermal properties, mechanical properties and toughness for the specific application end use.

Still another object of the present invention is to prepare fiber reinforced composites having particular utility in aerospace applications.

Still other objects and advantages will be apparent from the application.

As shown in the examples which follow, applicant has discovered a new method for preparing novel polymers wherein it is now possible to obtain both high temperature performance and high toughness, i.e., applicant has discovered a means to uncouple the usual temperature/toughness balance relationship. In particular, in a preferred embodiment applicant has prepared polymers having the following property set:

Glass transition temperature, Tg=175° C. (DSC)
Fracture toughness, $K_q$=2.5 KSI $\sqrt{in}$ (Compact Tension)

$$\text{Flex modulus, } E = \begin{cases} 390 \text{ KSI (Dry @ R.T.)} \\ 350 \text{ KSI (Wet @ 200° F.)} \end{cases}$$

Water gain, $\Delta W/W_o$=1.45% (saturation)
In other examples, applicant has also shown that

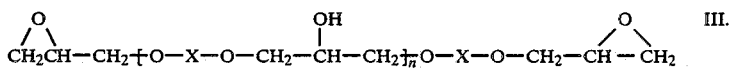

and

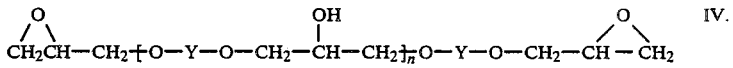

wherein if the phenol compound is HO—X—OH, then the diepoxide is chosen from the structure of formula III or IV and if the phenol compound is particular polymers, having particular ranges of stiff segments and flexible segments, possess truly extraordinary properties, especially relating to solvent resistance.

Such polymers may, as shown particularly in the Illustrative Embodiments, have unexpected solvent resistance which are synergistic improvements from the prior art.

DETAILED DESCRIPTION OF THE INVENTION

Figure 1:
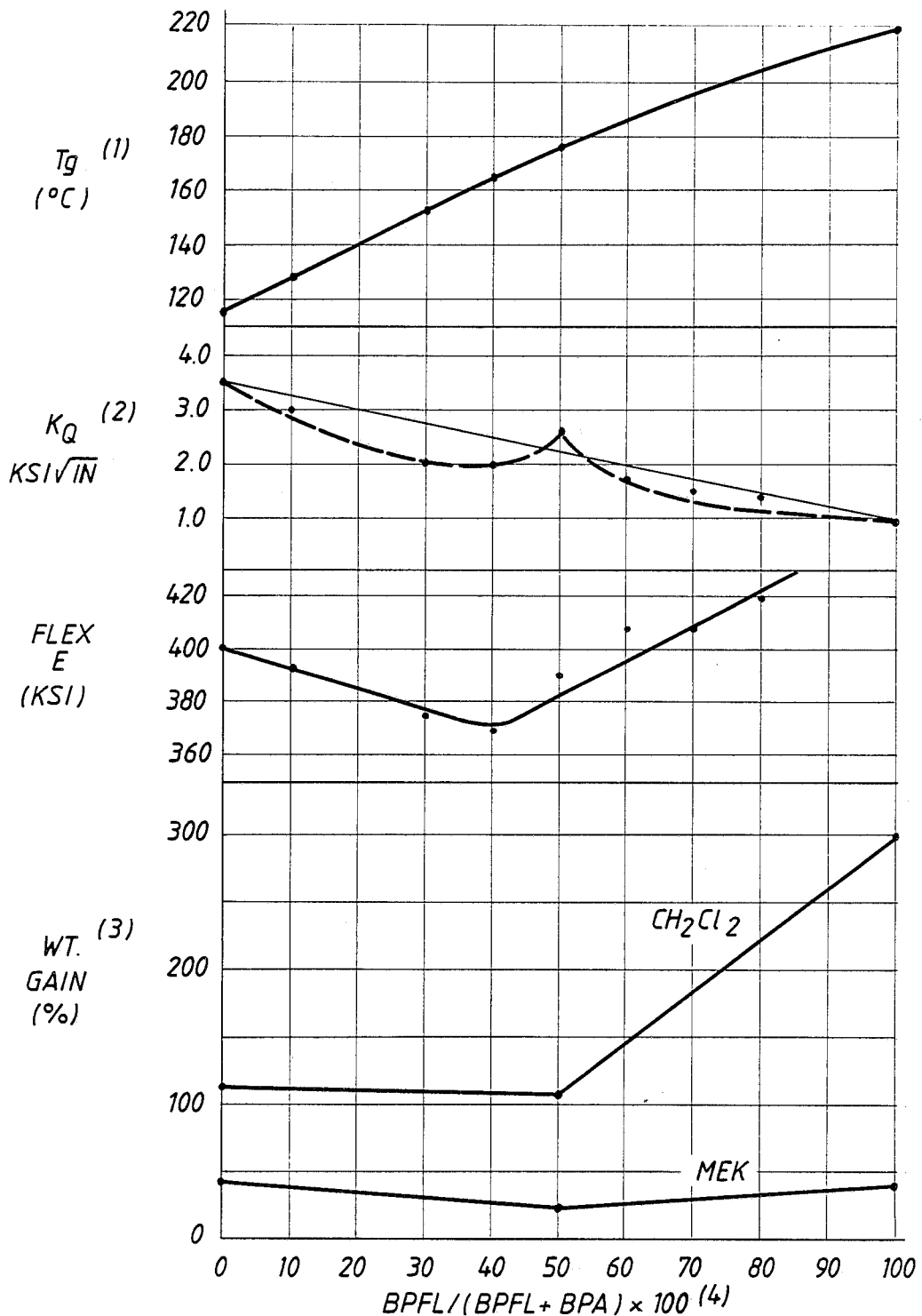
Figure 2:
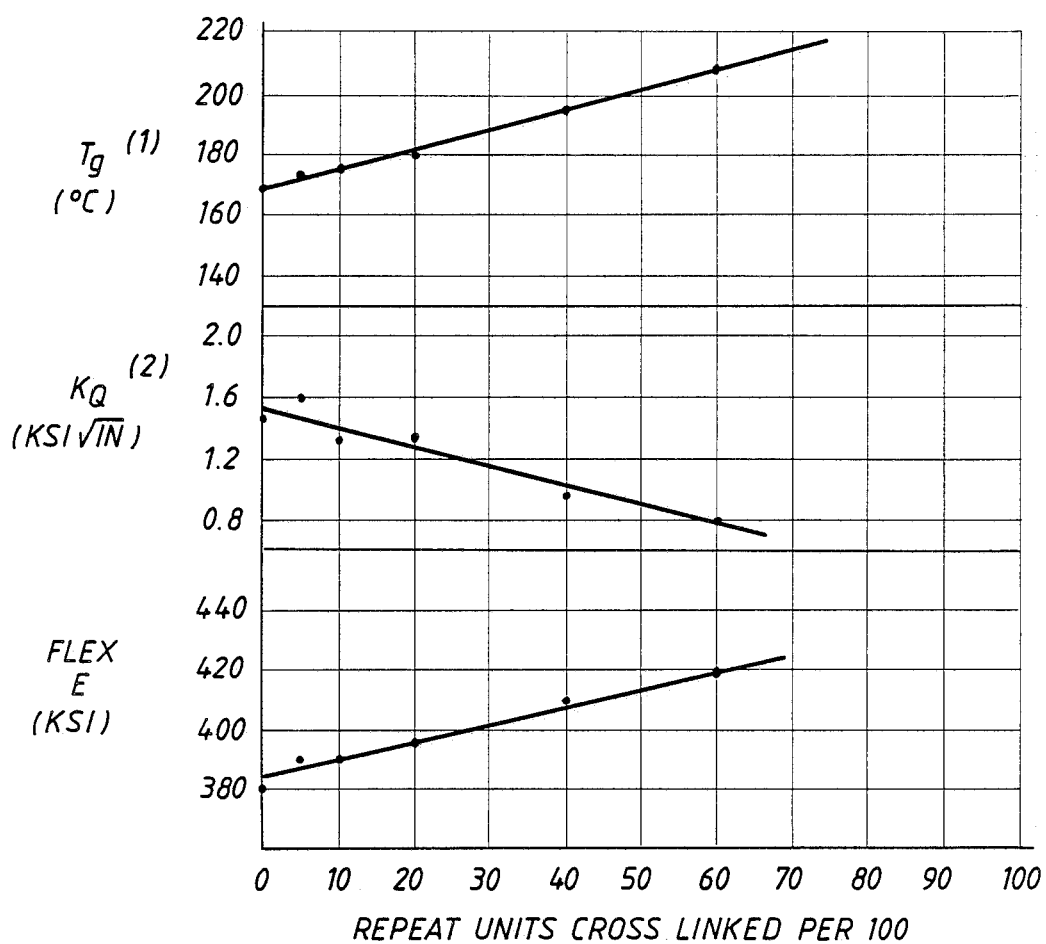

There are two basic aspects to the present invention—one involves the process for making certain thermoplastic polymers and the other involves the polymers as compositions-of-matter.

I. Process

In the broad sense, the present invention relates, as a minimum, to the mixture of a diphenol component and a diepoxide component to make a prepolymer composition, which may be stored for later reaction or which may be reacted with a condensation catalyst.

A. Diphenol Component

In a preferred embodiment the diphenol components employed herein have the structure HO—X—OH or HO—Y—OH where "X" represents the stiff segment specified above and "Y" represents the flexible segment specified above.

As a practical matter, it is preferred that the diphenol component contain the stiff segment, i.e. that the phenol component be HO—X—OH. The reason for this is that it is easier to synthesize the diphenol component (containing the relatively large number of stiff units) than it is to glycidate the corresponding diphenol compound. In particular, it is preferred to employ diepoxides based on BPA and use diphenol compounds based on the less common compounds. However, in certain cases it may be preferable to have the stiff segment, X, in the diepoxide component since the diepoxide may have a lower melting point than the diphenol component, resulting in an easier thermoplastic polymer synthesis, especially if it is desired to perform the synthesis in the melt as opposed to a solution preparation.

Preferably it is desired that the diphenol compound be meta or para derivatives as opposed to an ortho structure.

An important aspect of the present invention is the selection of stiff units and flexible units such that the resulting polymer molecules have the appropriate type and ratio of stiff units to flexible units.

By use of the term "flexible units" are meant those units that permit rotation at an angle. Examples of such flexible units are

| Broad group | Examples | | | |
|---|---|---|---|---|
|  |  |  |  | |
|  |  | | | |
|  |  | | | |

| Broad group | Examples |
|---|---|
|  | 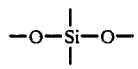 |
|  | |
|  |  |

The stiff units are selected from the group consisting of substituted or non-substituted aromatic rings, cycloaliphatic rings and heterocyclic rings. The aromatic rings are inertly substituted or un-substituted benzene radicals. Substituted benzene radicals have substituents which do not interfere in the process independently selected from the group consisting of Cl, Br or $C_1$-$C_5$ alkyl groups. Annulation of benzene rings gives rise to

| | | |
|---|---|---|
| naphthalene | 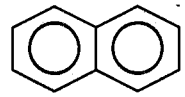 | (SU = 2), |
| anthracene | 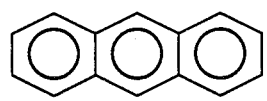 | (SU = 3) and |
| phenanthrene | 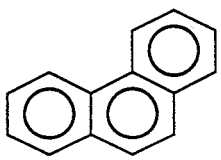 | (SU = 3), | and the like.

The cycloaliphatic rings are substituted or un-substituted $C_5$ or $C_6$ hydrocarbon radicals. Substituted cycloaliphatic rings are analogous to substituted aromatic rings. Un-substituted rings include, by way of example, cyclopentane, cyclohexane and cyclohexene. Annulation of cycloaliphatic rings gives rise to

| | | |
|---|---|---|
| decalin | 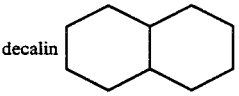 | (SU = 2) |
| [2.2.2]bicycloctane | | (SU = 3) |
| norborane | | (SU = 3) |
| adamantane ($C_{10}H_{16}$) |  | (SU = 4) | and the like.

The term heterocyclic rings refers to substituted or un-substituted 5-6 membered heterocyclic radicals.

Examples of 5-6 membered heterocyclic radicals are radicals of pyrrole  and pyridine 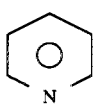

furan 

thiophene 

imidazole 

oxazole 

thiazole 

Annulation of heterocyclic rings with aromatic rings give rise to dibenzothiopene 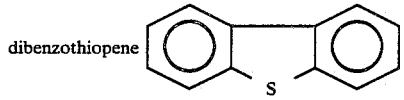

(SU = 3), carbazole 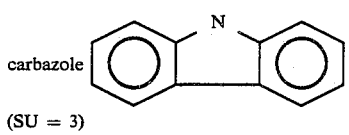

(SU = 3)

and the like.

Regarding the selection of heterocyclic structures, O and S heterocycles are generally suitable. In the case of N derivatives, however, care must be exercised such that the N is not strongly basic so that homopolymerization of the epoxide occurs. For example,

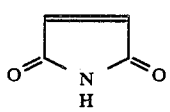

is suitable, but

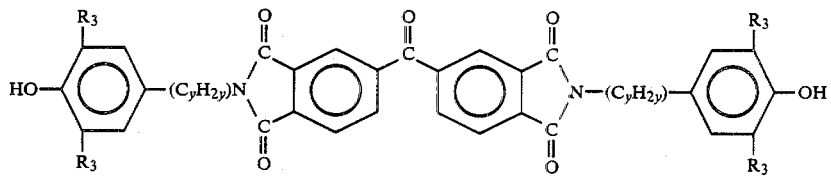

may not be suitable by itself (however the carbazole analog is suitable since the N is not strongly basic there).

One group of diphenol components particularly useful herein are those mentioned in U.S. Pat. No. 3,546,165. Specifically, those useful components are those phenoxy compounds of the formula where each $R_2$ substituent is indpendently selected from H, Cl, Br or $C_1$-$C_5$ alkyl and Z is a substituent having flexible units (FU or FU') and stiff units (SU or SU') where Z represents a gem-bivalent radical having 1 to 2 aromatic hydrocarbon rings and a gem-bivalent non-aromatic ring selected from the group consisting of a ring of 5 carbon atoms, a ring of 6 carbon atoms one of which carbon atoms may bear an oxo oxygen atom, and a ring of 5 carbon atoms and one oxygen atom, said gem-bivalent non-aromatic ring being fused to said aromatic hydrocarbon rings. Particularly useful are those components where Z is Specific examples include the following bisphenols:
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone,
9,9-bis(4-hyroxyphenyl)phenanthrone.
Other useful bisphenols include phenolphthalein,
9,9-bis(4-hydroxyphenyl)-9,10-dihydroanthracene,
9,9-bis(4-hydroxyphenyl)-10,10-diphenyl-9,10-dihydroanthracene,
3,3-bis(4-hydroxyphenyl)-4,5-benzodihydrofuran, and the like.

Another group of diphenol components useful herein are the imides represented by the formula wherein each of $R_3$ is the same or different (lower) alkyl group of from one to four carbon atoms; and y has a value of from 0 to 3. Such diphenol compounds are disclosed in U.S. Pat. No. 3,821,162 and reported by J. E. McGrath, 29th National SAMPE Symposium, Apr. 3-5, 1984, page 447.

Still another group of diphenol compounds are those based on phthalocyanine. Such compounds include the following:

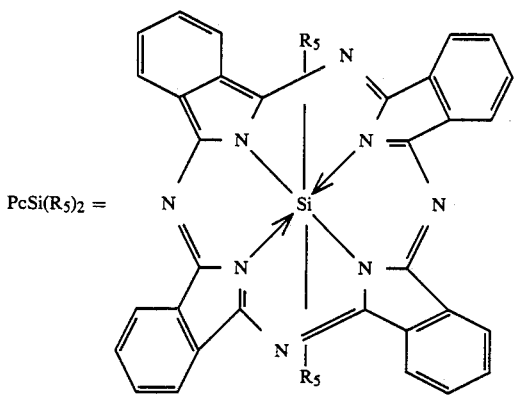

(a) $R_5$ = OH

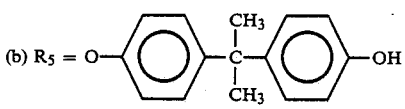

Still another group of diphenol compounds are those shown below. Additional aromatic, cycloaliphatic or heterocyclic rings may be annulated as desired:

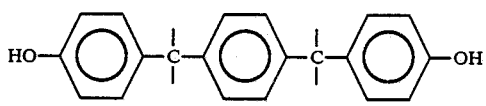
(SU = 3, FU = 2)

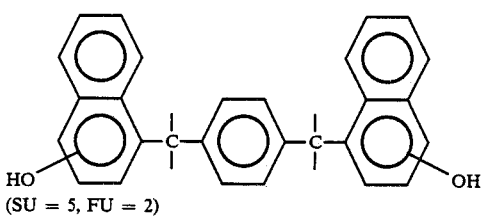
(SU = 5, FU = 2)

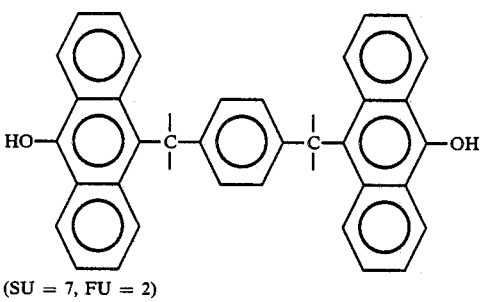
(SU = 7, FU = 2)

This particular group of diphenol compounds are distinguished from diphenol compounds such as BPA and the like, by the presence of 2 or more flexible units

If desired, the diphenoxy compounds described above may be substituted in part (or even in whole in certain cases) with other diphenols, represented by the general formula

in which R and $R^1$ when taken collectively with the connector carbon C are selected from the group consisting of cyclohexyl and alkyl-substituted cyclohexyl, and when taken separately are from the group consisting of hydrogen, alkyl, cyclohexyl, phenyl, alkyl-substituted cyclohexyl, alkyl substituted phenyl, halogen substituted cyclohexyl and halogen substituted phenyl groups with the total number of carbon atoms in the group or groups attached to said connector carbon atom not exceeding eighteen and the number of carbon atoms in any of said alkyl substituent groups not exceeding six. The preferred phenols have the hydroxyl groups in the 4,4' positions, but compounds with hydroxyls in the 2,2', 3,3', 2,4', and other arrangements may also be used. R and $R^1$ suitable are methyl, ethyl, isobutyl, n-nonyl, n-heptadecyl and the like. Other dihydric phenols may also be employed, excepting those which have two hydroxyl groups in ortho positions on a single benzene ring.

The dihydric phenol employed in the process of this invention may be substantially 100 percent pure, or may be a technical grade of somewhat lower purity. Concentrates of dihydric phenols containing, for example, 90 to 100 percent of the pure compound may be used.

B. Diepoxide Component

The second reactant in the condensation process, the diepoxide, is a compound having two vicinal epoxide groups (oxirane rings) in terminal (or optionally nonterminal) positions in the molecule, usually in the form of an oxygen atom bound to two terminal carbons of an alkyl group, though the epoxide may also be on a ring, such as a cyclohexyl ring. Suitable diepoxides are terminal diepoxyalkanes, e.g., 1,2-epoxy-3,4-epoxybutane, 1,2-epoxy-5,6-epoxyhexane, 1,2-epoxy-7,8-eoxyoctane and the like. Others are terminal diepoxides containing ether linkages, such as bis(2,3-epoxypropyl)ether and bis(2,3-epoxy-2-methylpropyl) ether; diglycidyl ethers of alpha,omega glycols such as the diglycidyl ethers of ethylene glycol, trimethylene glycol, and tetramethylene glycol; and diglycidyl ethers of dihydric phenols.

Diglycidyl ethers of the dihydric phenols referred to above are generally suitable for use in this invention. One may suitably use the diglycidyl ether of the same phenol which is employed as the other reactant. Thus, for example, bisphenol fluorenone is suitably condensed with diglycidyl ether of bisphenol fluorenone. Useful resins can also be prepared by condensing a dihydric phenol with the diglycidyl ether of a different dihydric phenol. For example, useful condensation products have been prepared according to this invention from the diglycidyl ether of bisphenol A and the dihydric phenol prepared from phenol and fluorenone.

In preparing the products of this invention the epoxy reagent may be a pure diepoxide or a crude mixture containing a substantial proportion of diepoxide, e.g., 70% or more. It is important, however, that the crude reagent is free of monoepoxide and of monohydric alcohol or phenol. The polyepoxides used herein have the structure III or IV, as shown in the Summary of Invention. The number "n" has a value of 0 to about 6, preferably 0 to about 2, more preferably zero.

A particularly preferred diepoxide is the diglycidyl ether of BPA. Such diepoxides are available from Shell Chemical Company as EPON® resins 825 and 828. Shell EPON Resin 825 is an essentially pure diepoxide of BPA (where n=0) while EPON Resin 828 is a diepoxide of BPA having a slightly higher average molecular weight and containing a small amount of n=1.

C. Selection of Stiff Units and Flexible Units for Stiff Segments and Flexible Segments A key aspect of the present invention is the selection and location of the stiff units (SU and SU') and flexible units (FU and FU') for the stiff segments (X) and flexible segments (Y). As discussed above, the stiff segment (X) may be located in either the diphenol component or diepoxide component or in both components. For ease of synthesis it is preferred that the stiff segment be in either the diepoxide component or the diphenol component. The selection will depend upon the particular components to be employed. For example, since the diepoxide of BPA is readily available, it may be preferable to use such a resin in the synthesis. Since the diepoxide of BPA has one flexible unit and two stiff units, it has an SU'/FU' of 2/1 or 2 and will therefore be the flexible segment Y. Then one must use a diphenol component having sufficient number of stiff units (SU) and flexible units (FU) such that the ratio $$\frac{\frac{a}{a+b} SU + \frac{b}{a+b} 2}{\frac{a}{a+b} FU + \frac{b}{a+b} 1}$$

is greater than 4. Where a/a+b is 0.5 then $$\frac{0.5\, SU + 1}{0.5\, FU + .5} > 4$$

and therefore SU>4FU+2
For example, the bisphenol of fluorenone has five stiff units and zero flexible units. Accordingly, the reaction product of a 50:50 mixture of the bisphenol of fluorenone and the diglycidyl ether of BPA has a ratio of
SU/FU of 5/0 and a ratio of SU'/FU' of 2/1
The average of $$\frac{\frac{a}{a+b} SU + \frac{b}{a+b} SU'}{\frac{a}{a+b} FU + \frac{b}{a+b} FU'} \text{ is}$$

$$\frac{0.5 \times 5 + 0.5 \times 2}{0.5 \times 0 + 0.5 \times 1} = 7,$$

which is the average number of total stiff units divided by the average number of total flexible units.

More particulars on these ranges and selections are found in the discussion of the Structures of the Resulting Polymers.

D. Catalyst and Reaction Conditions

The condensation reaction between the diphenol component and the diepoxide component requires the presence of a condensation catalyst, typically a basic condensation catalyst. The catalyst may, for example, be added as a concentrated aqueous solution of sodium or potassium hydroxide or a sodium salt of a phenol. One may also use halides, carboxylates or other nucleophiles. It is sometimes desirable to use as catalyst a sodium salt of the same dihydric phenol which is used as a reactant. These salts are generally solids which are dissolved in the reaction mixture. It has been found that very satisfactory results are also obtained when using concentrated aqueous sodium hydroxide or benzyltrimethyl ammonium hydroxide. When the catalyst is added as an aqueous solution, a concentrated solution is used since it is not desirable to have more than a small amount of water present in the reaction mixture.

The concentration of catalyst present during the condensation reaction must be held to a low value; otherwise branched polymers of low impact value are produced. However, it has also been found that reaction rates increase proportionately with catalyst concentration. The useful range of catalyst concentration is from 0.0001 to 0.100 mole per mole of the contained bisphenol. For best results the concentration is preferably between 0.001 and 0.010 mole per mole. It may occur that some of the catalyst reacts with impurities in the reactants. This results in a reduction of the rate of reaction and can stop the reaction prematurely. Adding a further amount of catalyst then permits the reaction to continue. It has been found that basic catalyst reacts with saponifiable chlorine if the latter is present in the diglycidyl ether reactant. It is therefore useful to add initially an extra amount of catalyst, sufficient to react with such chlorine, to prevent slowing down of the reaction.

It is preferred to keep the water content of the reaction mixture as low as possible, preferably below 0.5% by weight, more preferably below 0.2% by weight, and still more preferably below 0.12% by weight. In any event, the water content is to be maintained so as not to exceed about 1 percent by weight.

Careful control of the ratio of dihydric phenol and diglycidyl ether in the reaction mixture is of greatest importance in order to obtain a product having the desired characteristics. When technical grades of one or several reagents are employed, the correct ratio is maintained by determining the epoxy equivalence and the phenolic hydroxide equivalency of the reagents and carrying out the reaction with a mixture which contains not less than 0.90 phenolic hydroxide group per epoxide group and not more than 1.04 phenolic hydroxide group per vic epoxide groups

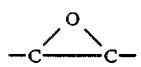

Best results are obtained with phenolic hydroxide/epoxy ratios in the range from 0.94 to 1.0 A slight excess of epoxy groups is preferred to a small excess of phenolic hydroxyl groups. When the catalyst employed is a basic salt of a dihydric phenol, then the phenol present in the catalyst is considered part of the phenolic reagent for purposes of calculating the proper ratio of reactants. Similarly, when the technical grade of the diepoxide contains some saponifiable chlorine, the chlorohydrin groups are considered the equivalent of epoxy groups since they are converted thereto during the condensation reaction in the presence of a basic catalyst. It is also desired to keep the saponifiable chlorine content low.

The reaction is typically carried out in solution in a solvent which meets the following criteria: (1) It is capable of maintaining reactants and reaction products in solution, at reaction temperatures, in the concentrations employed. These concentrations generally range between 20 and 60 percent by weight of the total reaction mixture. When the original concentration is high, it is generally necessary to add additional solvent during the course of the reaction to reduce the viscosity of the mixture and to maintain the product in solution. (2) It does not react significantly with epoxide groups or phenolic hydroxyl groups. Water and alcohols, for example, tend to interreact with the reactants and are therefore not suitable as solvents. (3) It is readily and completely removable from the final reaction mixture to permit recovery of a resin substantially completely free of solvent. Desired high impact resistance is a property which requires complete removal of solvent. In the production of resin for use in molding, extrusion, and the like, solvent is removed from the reaction mixture. In the production of resin for surface coatings, the resin may remain associated with solvent until it is actually applied as a coating and the solvent is removed by evaporation under suitable conditions. (4) Its boiling point must be such that the reaction can be carried out at 75° to 150° C. at a practical pressure. The solvent may be a mixture of individual compounds.

Useful solvents which meet those criteria are, for example, certain ketones, halogenated hydrocarbons and ethers. Methyl ethyl ketone is a preferred solvent. Cyclohexanone, methyl isobutyl ketone and the other ketones may be used. Chloroform, 1,2-dichloroethane and other chlorinated hydrocarbons may be used, particularly in admixture with ketones. Ethers, such as dioxane, tetrahydrofuran, dimethoxyethane and lower alkyl (methyl or ethyl) ethers of ethylene glycol are suitable, alone or in admixture with ketones. Other solvents which meet the above criteria may be employed if desired, such as N-methyl pyrrolidone.

While in the examples which follow the synthesis was performed in solution, it is also possible (and desirable in some cases) to do the synthesis in the absence of solvent, i.e. as a melt. In such cases it may be desirable to use the diepoxide containing the stiff segment since the melting point of diepoxide component is usually much lower than the melting point of the corresponding diphenoxy component.

A necessary process step for obtaining solid resin of high impact resistance suitable for molding or other forming is the complete removal of solvent from the resin mass.

II. Resulting Polymers

A. Structures

As mentioned above, a key aspect of the present invention is the selection and location of the stiff units (SU and SU') and the flexible units (FU and FU') for the stiff segments (X) and flexible segments (Y). Great latitude is provided for the selection and location of the particular components. For the most part the properties and performance of the resulting polymers depend primarily on the relative number of stiff units and flexible units (each such unit being assigned a value of one). However, there are certain important ratios and values that need to be followed.

Note that it is not necessary that the segments contain flexible units. For example, BPFL does not contain flexible units and is perfectly satisfactory.

The first important ratio is the average number of total stiff units divided by the average number of total flexible units. This ratio must satisfy the equation:

$$\frac{\frac{a}{a+b}SU + \frac{b}{a+b}SU'}{\frac{a}{a+b}FU + \frac{b}{a+b}FU'} > 4$$

Preferably this ratio is greater than 4 and less than about 20. More preferably this ratio is greater than 5 and less than 10. This ratio is important because it is an important factor in determining the Tg, or heat resistance of the polymer.

The second important ratio is that SU/FU must be equal to greater than SU'/FU', preferably greater. In other words, the stiff segment (X) must have an equal or higher ratio of SU/FU than the flexible segment (Y) ratio of SU'/FU'. This is important because it helps determine the Tg/toughness balance. Preferably SU/FU > SU'/FU' + 0.5.

In a preferred embodiment SU'/FU' is between 1 and 4, preferably between 2 and 3. For example, where it is preferred to use the diglycidyl ether of BPA, the SU'/FU' ratio is 2/1 or 2, and when the diphenoxy compound used is the bisphenol of fluorenone, the ratio of SU/FU is 5/0 or infinity, and accordingly, SU/FU > SU'/FU'.

The third important ratio is the relative amounts of stiff segments and flexible segments, i.e. a/(a+b). In the broadest case the ratio of a/(a+b) is more than zero and less than or equal to 1. The preferred ratios of a/(a+b) are between about 0.2 and 0.8, more preferably between about 0.3 and 0.7, most preferably between about 0.4 and 0.6. It is shown in the examples which follow that a most preferred ratio of a/(a+b) is between about 0.4 and 0.6 with optimum overall properties (especially solvent resistance) occurring when the ratio of a/(a+b) is equal to 0.5.

B. Light Crosslinking

Another important aspect of the present invention relates to the light crosslinking of the thermoplastic polymer molecules to form the resulting polymer matrix. The concept and process for light crosslinking of such polymers is another novel and unobvious aspect of the present invention. In the broadest sense, light crosslinking refers to the crosslinking of between 1 and 50 out of each 100 repeat units to repeat units of other molecules, e.g. formulas I or II of said thermoplastic polymer. Preferably, the crosslinking density is between 2 and 20 out of 100, more preferably between about 3 and 10 repeat units per 100 repeat units.

"Light crosslinking" is distinguished from the normal crosslinking or curing of epoxy resins where the crosslink density approaches 100 (stoichiometric) molecules or repeat units per 100 molecules or repeat units.

There are basically three different techniques that may be used to obtain lightly crosslinked matrices. One technique involves the use of a slightly greater number of diepoxide groups than phenolic groups (see earlier section on I.D. Catalyst and Reaction Conditions). When using this technique the repeat units will crosslink through the reaction of the secondary hydroxyl groups with the remaining epoxide groups. Once the thermoplastic polymer is prepared, it may be used alone or with a reinforcing fiber in an FRC-type (fiber reinforced composite) composition, wherein the polymer mass is heated to an elevated temperature (e.g. above 170° C.) and held at that temperature for the necessary time (typically about 2 to about 24 hours) to obtain crosslinking.

Another technique to obtain light crosslinking is to incorporate an appropriate amount of tri- or higher functional expoxide or tri- or higher functional phenolic or amine in the preparation of the thermoplastic polymer. The crosslinking agent, when added as a separate component, replaces a portion of the phenolic component or the epoxide component, as desired. For example, if 20% crosslinking agent is used, then 20% of the phenolic component is replaced on an equivalent basis.

Examples of suitable multifunctional epoxide polymers include Epon® Resin 1031 and Epon® Resin DPS-164. Epon Resin DPS-164 has the general formula

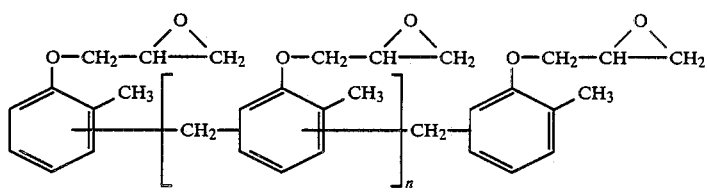

where n equals an averge of 3. Epon Resin 1031 has the structure

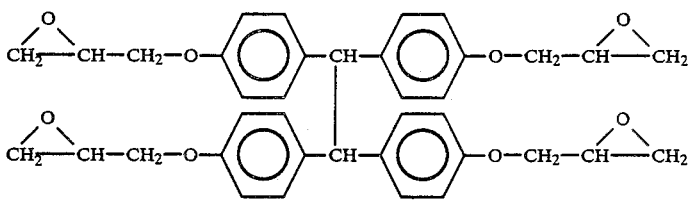

Other crosslinking agents include multifunctional amines such as EPON HPT ™ Curing Agents 1061 and 1062, having the molecular structure:

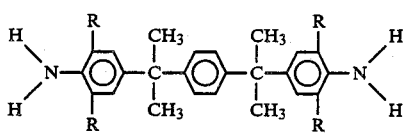

where R is H for CA 1061 and R is CH₃ for CA 1062.
Still other crosslinking agents include

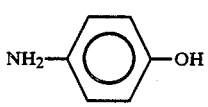

(PAP)

and

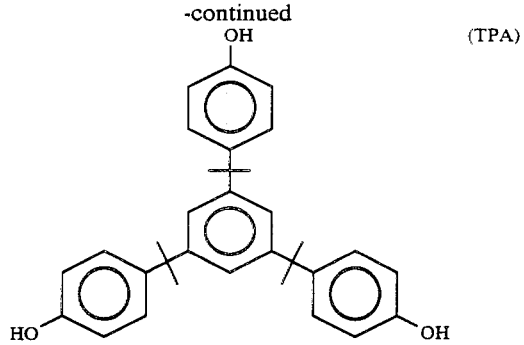

(TPA)

A third technique to obtain light crosslinking involves the addition of crosslinking agents, such as triepoxides, etc., to the resulting thermoplastic polymer. This technique is not preferred since it is more difficult to incorporate the crosslinking agent in the polymer after synthesis than before synthesis.

The amount of crosslinking agents chosen is selected to achieve the desired level of light crosslinking, as opposed to the normal crosslinking used for epoxy resins. Accordingly, when using a crosslinking agent such as EPON Resin 1031, the amount of equivalents used is 2 to 20%. Likewise, when the crosslinking agent is EPON HPT Curing Agent 1061, the amount of equivalents used is 5-50%.

C. Formulations and Composites

The composition optionally, but preferably for high-performance applications such as automotive and aerospace, contains a reinforcing substrate. Suitable reinforcing materials include, for example, glass fibers, carbon fibers, Kevlar, boron, calcium carbonate, talc, alumina, asbestos and the like. The preferred fibrous reinforcing material for high-performance applications is selected from the group consisting of glass fibers, carbon fibers, boron fibers and Kevlar fibers, with continuous carbon fiber being most preferred. The fibrous reinforcing material will be present in the composition in an amount effective to impart increased strength to the cured composition, generally from about 40 to about 95 weight percent, usually from about 60 to about 80 weight percent, based on the weight of the total composition.

The present composition can be applied to the fibrous reinforcing material from the melt or solution by methods known in the art. Among the various processes useful with the present invention include resin transfer molding (RTM), pultrusion, filament winding and the use of prepregs. Such methods are known in the art, and are disclosed, for example, in the Handbook of Composites, Lubin, Ed., Van Nostrand Reinhold Company, 1982, pages 321–532, and in the book by Delmonte titled Technology of Carbon and Graphite Fiber Composites, Delmonte, Van Nostrand Reinhold Company, 1981.

One method of current preferred interest involves the use of pre-pregs. In that system, the polymer composition/curing agent—impregnated substrate, or "prepreg", or a laminate prepared from a plurality of prepregs, is then cured. When the system is based on Epon® 825 resin and the bisphenol of fluorenone, the curing is typically accomplished at a temperature of about 150° to about 200° C. for about 1 to 16 hours under vacuum or under a presence of 1 atmosphere to 150 psi, to form the structural composite article.

D. Uses

The compositions of the present invention have particular application in the aerospace industry where the high performance obtainable with the present invention is required. In particular, RIM may be used to prepare large parts, such as helicopter blades. Pre-pregs may be used to prepare parts such as wings and the like. Filament winding may be used to prepare an entire fuselage, while pultrusion may be used to prepare parts having a constant cross section.

The invention composition can optionally include additives for control or modification of various properties of the composition in its cured or uncured state, including cure rate accelerators or retardants, tackifiers and the like.

To illustrate the present invention, the following illustrative embodiments and comparative examples are given. It is to be understood, however, that the embodiments and examples are given for the purpose of illustration only and the invention is not to be regarded as limited to any of the specific materials or conditions used in the specific embodiments.

As used in the following examples, Epoxy Resin A is a liquid glycidyl polyether of 2,2-bis(4-hydroxyphenyl)-propane having an epoxide equivalent weight of 170–174 and an average molecular weight of about 345.

Epoxy Resin B is a liquid glycidyl polyether of 2,2-bis(4-hydroxyphenyl)propane having an epoxide equivalent weight of 180–195 and an average molecular weight of about 380.

Epoxy Resin C is a solid glycidyl polyether of 2,2-bis(4-hydroxyphenyl)propane having an epoxide equivalent weight of 1650–2100 and an average molecular weight of about 2900.

The compositions were tested according to the following test procedures:

Flexural properties of neat resins were evaluated according to ASTM D790 method using 1/8 in. thick specimens. Specimens were tested both in Dry (at Room Temperature and ~75% R.H.) and Hot/Wet (after immersion in boiling water for 48 hours, test at 200° F., 5 min. equilibration time) conditions.

Fracture toughness, $K_q$, was measured using mini-compact tension specimens (see W. B. Jones, et al. Am. Chem. Soc., Div. Polym. Chem., Polym. Prepr., 22, 1981). All specimens were slotted to a Chevron shape and then precracked with a razer blade.

Tensile properties were measured according to ASTM D638 method.

Swelling in solvents was evaluated by measuring weight gain per unit of initial weight after immersion in solvent for a specified time at room temperature.

ILLUSTRATIVE EMBODIMENT I

In this example, a thermoplastic polymer composition according to the present invention was prepared having a phthalocyanine structure as the stiff segment. Initially 1,3-diiminoisoindoline was prepared from o-phthalonitrile by the method of Marks (see J. J. Marks, C. W. Dirk, T. Inabe and J. K. Schach, Jr., J. Am. Chem. Sci., 105 (6), 1539(1983)) to give a green solid with a melting point (m.p.) of 193°–194° C. in 50% yield.

A SiCl$_2$·phthalocyanine (PcSiCl$_2$) structure as shown below was then prepared from 1,3-diimino-isoindoline by the method of Marks:

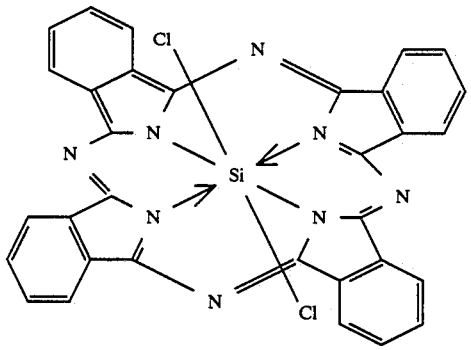

The purple solid was washed with chloroform, methanol, acetone and hexane to give product in 86% yield. For analysis the material was dried at 110° C. (1 mm) for 2 hours.

Ten grams of the above dichloride and 100 g of BPA, 6.7 ml of pyridine and 400 ml of o-dichlorobenzene were mixed under anhydrous conditions and stirred under nitrogen at 140° C. for 5 hours. The mixture was cooled, diluted with 400 ml of anhydrous THF and filtered. The filtrate was evaporated in-vacuo (water bath=60–70° C). to dryness. The residue was stirred with 1.3 L of 50% aqueous acetone to remove excess BPA, filtered, and washed with 2-100 ml portions of acetone to give 14.6 g (89%) of blue solid.

HPLC analysis (uncalibrated) showed the material to be about 92% pure. The remainder is higher molecular weight material (GPC) and believed from the Si-NMR spectrum to be BPAPcSiOSiPcBPA.

The resulting structure is shown below:

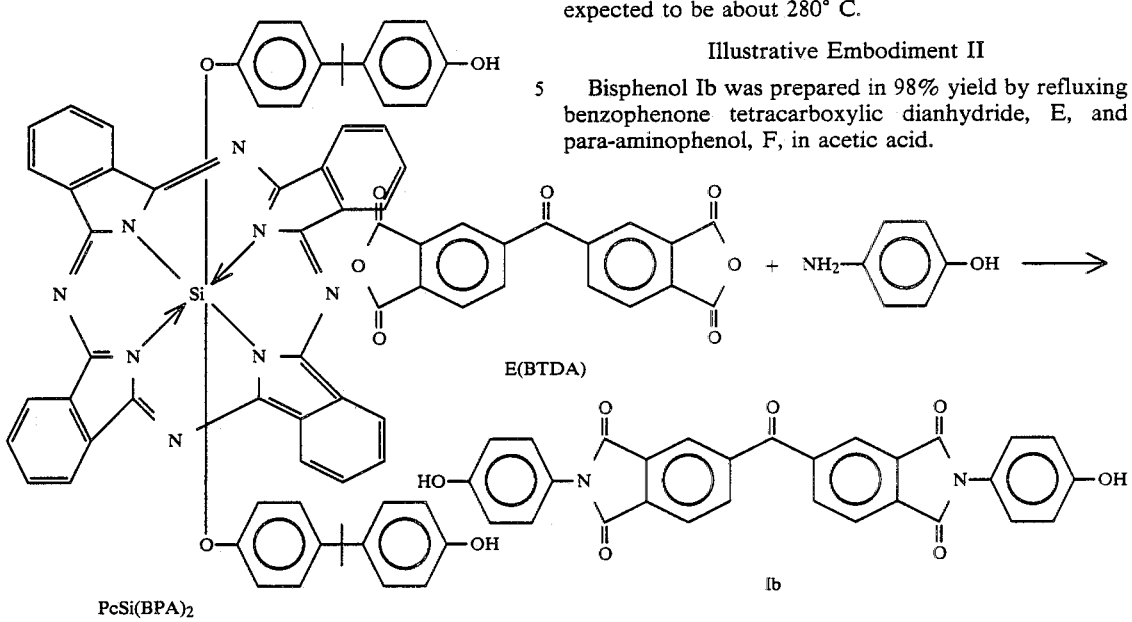

PcSi(BPA)₂

In the next step, varying amounts of the PcSi(BPA)₂ bisphenol were employed with Epoxy Resin A to prepare thermoplastic compositions according to the present invention. Recrystallized Epoxy Resin A, 8.824 mmol, dry N-methyl-2-pyrrolidone (NMP), 8 ml, NaBPA, 0.176 mmol, and 8.824 mmol of a mixture of BPA and PcSi(BPA)₂ were mixed under anhydrous conditions, and heated under N₂ at 110° C. for 5 hours. The mixture was cooled, evaporated at room temperature and 1μ pressure to dryness. The residue was extracted with acetone to constant $T_g$.

The results are presented below in Table 1:

TABLE 1

| Phthalocyanine (PcSi(BPA)₂) | | | | Solubility (% w, r.t.) | | |
|---|---|---|---|---|---|---|
| mmol | Mole Fraction | $\overline{M}_n$ | $T_g$ (°C.) | DMK | THF | NMP |
| 0 | 0.00 | 8,000 | 100 | >40 | >40 | >40 |
| 1.87 | 0.09 | 17,000 | 123 | 0.5 | 19 | >20 |
| 2.80 | 0.13 | — | 136 | 0.1 | 10 | >20 |
| 4.67 | 0.18 | 10,000 | 151 | 0.05 | 4 | >20 |

As shown above, the $T_g$ increases and the solubility decreases rapidly with phthalocyanine content. At a phthalocyanine mole fraction of 0.5, the $T_g$ would be expected to be about 280° C.

Illustrative Embodiment II

Bisphenol Ib was prepared in 98% yield by refluxing benzophenone tetracarboxylic dianhydride, E, and para-aminophenol, F, in acetic acid.

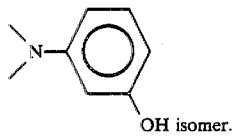

E(BTDA)

Ib

The above products also include the

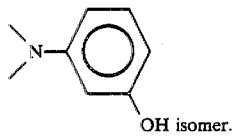
OH isomer.

Specifically, BTDA (E), 32.2 g, and 21.8 g of p-aminophenol were stirred in 300 ml of acetic acid at room temperature for 7 hours and then refluxed overnight. The mixture was cooled, filtered, and the solid washed with 800 ml of water. The material was dried at 180° C. for 6 hours to give 49.5 g (98% yield) of yellow solid, m.p. (DSC) ~394° C.

For analysis, the material was recrystallized from NMP-toluene, M.P. (DSC) 424° C. The IR spectrum of this material showed the presence of imide and phenolic groups and the absence of anhydride groups.

Next, Epoxy Resin A, 8.824 mmol, 8.824 mmol of bisphenol Ib, 0.176 mmol Na BPA, and 30 ml of NMP were mixed and stirred under N₂ at 120° C. for 24 hours. The reaction mixture was cooled and precipitated by pouring into ice water in a Waring blender to give 7.3 g (97%) of yellow solid after drying. The material had a $T_g$ of 173° which increased to 175° C. after washing with NMP. The $M_n$ was 10,800 (OSMOMETRY). Solubility in THF, CH₂CH₂ and Skydrol was nil, 1.5% in NMP. The material exhibits a crystalline m.p. ~320° C. which does not shift from heat up to cool down. TGA shows the material is generally stable up to 375° C., but exhibits very slow decomposition at 340° C. with consequent void formation during compression molding at that temperature. The material can be extruded, but void formation is extensive.

A similar run was made using 90%w Epoxy Resin A and 10%w Epoxy Resin C (EQ. WT.=1676) to give 7.7 g of polymer, $T_g$ (DSC)=157° C., $T_m$ (DSC)=320° C. Solubility in NMP=7.8%w.

Illustrative Embodiment III

Illustrative Embodiment III compares various systems according to the invention with other competing systems. System #1 (outside the invention) is based on a compilation of data for the diaminodiphenyl sulfone curing of the tetraglycidyl ether of methylene dianiline.

Systems 2, 3 and 4 are based on the copolymer from Epoxy Resin A and bisphenol-fluorenone (BPFL). To prepare the composition designated System #2, recrystallized Epoxy A, 3.000 g, BPFL, 3.0227 g, and monosodium BPA, 0.0441 g, were mixed with 16 ml of NMP and heated at 120° C. under $N_2$ for 5 hours. The cooled solution was poured into excess ice water, filtered, extracted with acetone and toluene, and dried to give 5.7 g (94% yield) of white solid, $T_g=162°$ C., mol. wt. (OSMOMETRY)=24,600, $[\eta]_{35°}$ $_{C.,NMP}=0.56$. Alternatively, System #2 may be prepared by mixing BPFL with Epoxy A at a mole ratio (P/E) of 1.04, adding catalyst and heating to 180° C., degassing at 1 Torr, and curing for 24 hours at 180° C.

System #3 involved melt polymerization of BPFL and Epoxy A at a P/E ratio of 0.96 with 0.18%m (basis Epoxy A) NaBPA catalyst. Reaction conditions were typically 190° C. for 24 hr.

System #4 involved melt polymerization of BPFL and Epoxy A under conditions identical to system #3 except that part of Epoxy A was replaced by an equivalent amount of Hycar ® CTBN such that the final product contained 10%wt Hycar CTBN (a butadiene rubber produced by B. F. Goodrich).

System 5 relates to a thermoplastic poly-(etheretherketone) matrix.

The results are presented below in Table 2. As shown in Table 2 by comparing System 2 with System 3, lightly crosslinking the epoxy/BPFL matrix significantly improves toughness ($K_q$) and tensile strength along with chemical resistance.

This approach has resulted in the development of a new copolymer with a controllable degree of crosslinking such that it could cover the thermoplastic-thermoset range, which should allow the optimization of the system. The chemistry for the preparation of these materials is shown in Illustrative Embodiment III. The copolymer of Epoxy Resin A and bisphenol-fluorenone (BPFL) exhibited a good balance between fracture toughness and $T_g$ values. In the present example, other important characteristics (e.g. water absorption and hot-wet properties) have been studied.

Water absorption was measured by the specimen's weight gain as a function of time. The polymer was immersed in boiling water. As was shown from the shape of the curve of absorption, saturation takes place at approximately 300 hours. The weight gain at saturation is equal to 1.45%, which is typical for high temperature performance resins rather than for flexibilized epoxy resins.

The hot-wet properties of the Epoxy Resin A/BPFL copolymer were studied after its immersion for 40 hours in boiling water. Flexural properties were measured at room temperature, 200° F. and 270° F. for dry and wet materials (see Table 3). All specimens exhibit yielding at approximately 5–6% of deformation. Specimens did not break at up to 10% strain in bending conditions with the exception of a few specimens which had large voids near the outer surface under the loading nose.

As shown in Table 3, the reduction in moduli with increasing temperature from 72° to 200° F. is minor and is practically the same for dry and wet materials indicating that in this temperature range the change in modulus can be considered primarily a function of temperature alone. At higher temperature, 270° F., the effect of moisture presence is more pronounced since the decrease in modulus for wet material is significantly higher than for dry material. A similar interpretation can be made with respect to the change in yielding stress as a function of

TABLE 2

| | | MATRIX MECHANICAL PROPERTIES | | | | | | |
|---|---|---|---|---|---|---|---|---|
| SYSTEM NO. | SYSTEM | $T_g$ (°C.) | SOL. % w, NMP | PROCESS$^{(a)}$ TP | TS | $K_q$ (psi in) | E (ksi) | $\epsilon^{(b)}$ (%) | $\sigma^{(b)}$ (ksi) |
| 1 | TGEMDA/DDS$^{(c)}$ | 210 | 0 | — | + | ~500 | 560 | ~2 | 16 |
| 2 | Epoxy Resin A/BPFL$^{(e)}$ | 162 | 15 | + | + | 1500 | 400 | ~2 | 8 |
| 3 | (a) Crosslinked | 175 | 0 | + | + | 2500 | 400 | >10 | 20 |
| 4 | (b) 10% w Rubber$^{(d)}$ | 145 | 1 | + | + | 3200 | 350 | >10 | 16 |
| 5 | PEEK | 145 | 0.1 | + | — | ~4000 | 500 | >10 | 15 |

$^{(a)}$TP = Thermoplastic, TS = Thermoset Processability; + means acceptable, − means unacceptable.
$^{(b)}$Flexural measurements.
$^{(c)}$Compilation data, approximate only. TGEMDA = TetraGlycidyl Ether of Methylene DiAniline, DDS = DiaminoDiphenyl Sulphone.
$^{(d)}$HYCAR CTBN.
$^{(e)}$Melt polymerization.

Illustrative Embodiment IV

The important factors affecting the development of new matrix resins for advanced composites are: toughness, moisture resistance, elevated temperature performance and improved processability. The importance of these factors invariably is the result of a particular deficiency in current resins relative to specific applications. Traditional methods of toughening epoxy resins by flexibilization or by introduction of rubber invariably result in the reduction of hot-wet properties of the resin. Thermoplastic matrices can have high toughness but usually suffer from chemical resistance of processability. An alternative approach is the development of "crosslinked thermoplastic" on the basis of epoxy chemistry, as disclosed and claimed herein.

temperature and moisture.

On the basis of these observations the following conclusions can be drawn. The water sorption at saturation of EPON/BPFL copolymer is relatively low. The copolymer retains good mechanical properties under hot-wet conditions up to 200° F. and therefore can be considered a good candidate for aerospace applications.

TABLE 3

| Flexural Properties of Epoxy Resin A/BPFL Copolymer | | | | | |
|---|---|---|---|---|---|
| | E, ksi | | $\sigma_y$, ksi | | $\epsilon_{max}$, % |
| Temp., °F. | D | W | D | W | D | W |
| 72 | 380 | 380 | 18.7 | 18.0 | >10 | >10 |
| 200 | 350 | 365 | 15.5 | 13.2 | >10 | >10 |

TABLE 3-continued

Flexural Properties of Epoxy Resin A/BPFL Copolymer

| Temp., °F. | E, ksi | | $\sigma_y$, ksi | | $\epsilon_{max}$, % | |
|---|---|---|---|---|---|---|
| | D | W | D | W | D | W |
| 270 | 285 | 170 | 8.7 | 3.7 | >10 | >10 |

D - Dry
W - Wet (After Immersion for 40 hr in Boiling Water)

Illustrative Embodiment V

Illustrative Embodiment V deals with the effect of small changes in crosslink density on polymer performance. The components employed were BPA, BPFL and Epoxy Resin A. The phenol to epoxy resin ratio was varied in order to vary the crosslink density from 0% (1:1 ratio of phenol to epoxy) to about 10% (0.9:1 ratio of phenol to epoxy). The syntheses of these polymers were similar to those prepared in Illustrative Embodiment III except as shown in Table 4.

The preparation conditions and test results are presented below in Tables 4 and 5. As may be seen from Table 5, there is the expected increase in glass transition temperature (Tg) from 166°–172° C., but the mechanical properties are roughly constant with the fracture toughness at a high value of 2330±90 psi. $\sqrt{\text{in}}$. Closer examination of the fracture toughness data indicates an optimum value in the P/E range of 0.96–0.98. Similar data clearly shows reduced values at higher P/E ratios.

TABLE 4

| Experiment** | P/E | Catalyst % m* | Temp. (°C.) | Time (hrs.) |
|---|---|---|---|---|
| 78 | 1.00 | 0.16 | 190 | 24 |
| 82 | 0.98 | 0.18 | 190 | 24 |
| 75 | 0.96 | 0.16 | 180 | 24 |
| 83 | 0.94 | 0.18 | 190 | 24 |
| 80 | 0.90 | 0.24 | 190 | 24 |

*Moles NaBPA/moles epoxide.
**⅛" castings in glass mold by melt polymerization at prescribed conditions.

TABLE 5

MECHANICAL PROPERTIES OF EPOXY RESIN A/BPFL COPOLYMER

| Experiment | Phenol/epoxy mol ratio | Crosslink[5] Density % | BPFL/BPA[4] mol ratio | Tg[1] (°C.) | E[2] (KSI) | $\sigma_y$[2] (KSI) | $\epsilon_y$[2] (%) | $K_q$[3] psi in ½ |
|---|---|---|---|---|---|---|---|---|
| 78 | 1.00 | 0 | 0.90 | 166 | 360 | 11.3 | 6.8 | 2300 |
| 82 | 0.98 | 2 | 0.90 | 168 | 390 | 11.2 | 6.5 | 2450 |
| 75 | 0.96 | 4 | 0.90 | 169 | 360 | 11.0 | 6.4 | 2350 |
| 83 | 0.94 | 6 | 0.90 | 172 | 380 | 11.2 | 7.1 | 2200 |
| 80 | 0.90 | 10 | 0.90 | 172 | 385 | 11.2 | 6.9 | — |

[1] DSC measurement
[2] Tensile measurement
[3] Mini compact tension
[4] Ratio of BPFL to BPA moieties irrespective of source
[5] % Branched epoxy groups/total epoxy groups

Illustrative Embodiment VI

Illustrative Embodiment VI deals with the preparation of polymers from 9,9-bis(4-hydroxyphenyl)-10-anthrone (BPAQ) and Epoxy Resin A. The BPAQ was prepared by reacting anthraquinone (AQ) with a 13 molar excess of phenol in the presence of 1.05 molar trifluoromethanesulfonic acid (triflic acid) for 60–90 minutes at 100° C. BPAQ was recovered in 40–45% yield by neutralizing the reaction mass with 20%wt aqueous NaOH and filtering the precipitate (which was 85–95% BPAQ). Purification involved recrystallization from boiling dimethylsulfoxide and then extraction of residual AQ with boiling acetic acid. The 99.5% pure BPAQ melts at 319°–321° C. and has been identified by $C^{13}$ NMR analysis.

The diglycidyl ether of BPAQ (DGBPAQ) was prepared from BPAQ in a standard prep procedure. To prepare the polymers of the present invention, BPA (0.96 mole) and DGBPAQ (1.00 mole) were mixed with NaBPA (0.0012 mole), melted at 180° ($N_2$), poured into a glass mold and cured at 180° C. for 1 hour and 190° for 23 hours, Tg=175° C. (DSC).

Flexural and Fracture Toughness Data for BPA/BPAQ Polymer Matrix

E = 400 KSI
= $\sigma$ Yield = 18.5 KSI
= $K_q$ = 2400 psi $\sqrt{\text{in}}$ $\epsilon$ > 8% (no break)

In a similar manner BPFL was reacted with DGBPAQ and NaBPFL catalyst at 210° C. for 24 hours, resulting in a polymer having a Tg=225° C.

Illustrative Embodiment VII

Illustrative Embodiment VII deals with the preparation of Bisphenol-Fluorenone (BPFL)-Epoxy Resin A copolymer/graphite fabric composite. BPFL and Epoxy Resin A were mixed at 180° C. and then cooled to room temperature under conditions similar to that in Illustrative Embodiment III. At room temperature this product is in solid form and it has practically unlimited shelf life. The composite was prepared by a melt fusion method using a vacuum bag molding technique. The BPFL-Epoxy Resin A compound was powderized and placed between layers of graphite fabric (Magnamite Graphite Fabric Style AS 370-8H). It was covered with release fabric, bleeder and vacuum bag. Curing conditions were the following: vacuum: 30 in Hg, top pressure: 90 psi, temperature: 180° C. for 1 hour and 190° C. for 16 hours. This resulted in a practically void free composite containing 62% fiber by volume.

The following mechanical properties were measured: Flexural (ASTM D790), Short Beam Shear (SBS) strength, Mode I Interlaminar Fracture Toughness (see P. E. Keary and L. B. Ilecevicz, J. Comp. Mater., Vol. 19, March 1985, pp. 154–177). This data along with the data from the literature for conventional epoxy matrix-/graphite fabric composites are presented in Table 6. As can be seen, the BPFL-Epoxy Resin A matrix composite has flexural and short beam shear properties comparable to conventional epoxy matrix composites, while its delamination fracture toughness is an order of magnitude higher than for conventional epoxy matrix composites. That high level of fracture toughness in combination with good traditional properties and high glass transition temperature (172° C.) allows one to consider the BPFL-Epoxy Resin A copolymer as an excellent matrix material for high performance composite materials.

TABLE 6

| | BPFL-Epon Resin A/ Graphite Composite | Conventional Epoxy/ Graphite Composite |
|---|---|---|
| Flexural Strength [KSI] | 134 | 130[a] |
| Flexural Modulus [KSI] | 9100 | 9500[a] |
| SBS Strength [KSI] | 9.7 | 9.0[a] |
| Delamination Fracture Toughness [in.lbs/in²] | 11.0 | 1.3[b] |

[a]Hercules Product Data Sheet.
[b]J. T. Hartness, SAMPE, January 1983.

Illustrative Embodiment VIII

In Illustrative Embodiment VIII, various polymers were prepared according to the present invention in syntheses similar to those used in Illustrative Embodiment III. The various formulations and test results for cured compositions are shown below in Table 7.

TABLE 7

| Phenol | Epoxy | P/E | Cat (%)[1] | Cure[2] | Gel (%) | Tg (°C.)[3] | % WT GAIN[4] | | | FLEX DATA | | | $K_q$ (psi in) |
|---|---|---|---|---|---|---|---|---|---|---|---|---|---|
| | | | | | | | MEK | $CH_2Cl_2$ | $H_2O$ | E (KSI) | (KSI) | ε (%) | |
| BP | DGBPFL | 0.96 | 75 | B | 100 | 194 | 7 | 42 | | 340 | 16.5 | >8 | 1600 |
| BPA | DGBPFL | 0.96 | 75 | A | 86 | 175 | | | | 400 | | | 1700 |
| BPA | DGBPAQ | 0.96 | 50 | A | 80 | 175 | | 112 | | 400 | 18.5 | >8 | 2400 |
| BPC | DGBPFL | 0.96 | 75 | B | 94 | 185 | 23 | 75 | 2.2 | 440 | 16.7 | 4 | 1500 |
| HFBPA | DGBPFL | 0.96 | 75 | A | 96 | 188 | | 200 | | 400 | 20.5 | 7 | 1400 |
| BPFL | DGBPA | 0.96 | 75 | A | 98 | 175 | 25 | 113 | 1.8 | 390 | 20.5 | >8 | 2500 |
| BPFL | DGBPFL | 0.96 | 75 | B | 32 | 222 | 39 | 303 | 1.5 | | | | 700 |
| BPFL | DGBPAQ | 0.96 | 30 | B | 46 | 222 | | | | | | | |

| STRUCTURE LEGEND | |
|---|---|
| SYMBOL | CHEMICAL NAME |
| BP | 4,4'-Dihydroxybiphenyl |
| BPA | 2,2-Bis(4-hydroxyphenyl)propane |
| BPC | 4,4'-Dihydroxybenzophenone |
| HFBPA | 1,1,1,3,3,3-Hexafluoro-2,2-bis(4-hydroxyphenyl)propane |
| BPFL | 9,9-Bis(4-hydroxyphenyl)fluorene |
| BPAQ | 9,9-Bis(4-hydroxyphenyl)-10-anthrone |
| DGBPA | 2,2-Bis[4-(2,3-epoxypropoxy)phenyl]propane |
| DGBPFL | 9,9-Bis[4-(2,3-epoxypropoxy)phenyl]fluorene |
| DGBP | 4,4'-Bis(2,3-epoxypropoxy)bisphenyl |
| DGBPAQ | 9,9-Bis[4-(2,3-epoxypropoxy)phenyl]-10-anthrone |

[1]100% = 0.12% m, basis epoxide.
[2]Cure A is 190° C. for 24 hours, Cure B is 210° C. for 24 hours.
[3]DSC.
[4]24 hours at room temperature for MEK, $CH_2Cl_2$. Equilibrium for $H_2O$
[5]Mini-compact tension.

Also as part of this example, resin properties as a function of BPFL content, crosslink density and phenol/epoxide action are plotted. Some of the data are taken from the polymers shown in Table 7. Other data from similarly prepared polymers are also included.

FIG. 1 shows data for the basic BPA/BPFL system. BPA forms the flexible segments and BPFL the stiff segments. Initially, for the "zero" point, BPA was reacted with DGBPA. The BPA was gradually replaced with BPFL and so at the 50% point $$a(a+b)=0.50$$

the polymer was prepared by reacting BPFL and DGBPA in a ratio of about 0.96 to 1. After that point the DGBPA was gradually replaced with DGBPFL until at the 100% point the polymer was prepared by reacting BPFL with DGBPFL in a ratio of about 0.96 to 1. As may be seen, the a/(a+b) ratio plays an important role for both physical and mechanical properties. The minimum at 50% for solvent swelling and optimum for fracture toughness ($K_q$) are especially important for aerospace applications.

FIG. 11 displays data for the DGBPA/BPFL system with added crosslinking agent (EPON Resin 1031). The amount of crosslinking agent was increased in a series of polymers by replacing a portion of the DGBPA with Epon Resin 1031. As seen in FIG. II, glass transition temperature and flex modulus increase and fracture toughness ($K_q$) decreases with increasing crosslink density.

FIG. III shows data for the basic DGBPA/BPFL system as a function of phenol/epoxy ratio. As may be seen, it is important to run the reaction at a ratio near 0.96 to develop full fracture toughness ($K_q$)potential.

What is claimed is:

1. The composition comprising linear molecules having the repeating structures:

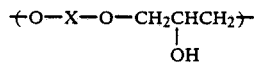
    I.

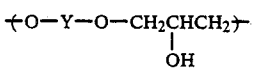
    II.

wherein:
(a) the segment X comprises stiff units (SU) and optional flexible units (FU) and has the structure —A—Z—Ar— where Ar is substituted or non-substituted benzene rings, optionally annulated with one or more additional benzene rings, and wherein Z represents a gem-bivalent radical having 1 to 2 aromatic hydrocarbon rings and a gem-bivalent non-aromatic ring selected from the group consisting of a ring of 5 carbon atoms, a ring of 6 carbon atoms, one of which carbon atoms may bear an oxo oxygen atom, and a ring of 5 carbon atoms and one oxygen atom, said gem-bivalent non-aromatic ring being fused to said aromatic hydrocarbon rings;

(b) "Y" represents a segment comprising stiff units (SU') and optional flexible units (FU') which stiff units and flexible units are interconnected;
(c) said stiff units, SU and SU', are independently selected from the group consisting of substituted and non-substituted aromatic rings and non-interfering heterocyclic rings;
(d) said flexible units, FU and FU', are independently selected from the group consisting of

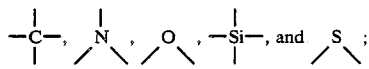

(e) the number of "X" segments in said molecules is "a", the number of "Y" segments in said molecules is "b", and the ratio of a/(a+b) is greater than zero and less than or equal to one;
(f) the number of stiff units and flexible units is selected such that the average number of total stiff units $$\left(\left(\frac{a}{a+b}\right)\cdot SU\right)+\left(\left(\frac{b}{a+b}\right)\cdot SU'\right)$$

divided by the average number of total flexible units $$\left(\left(\frac{a}{a+b}\right)\cdot FU\right)+\left(\left(\frac{b}{a+b}\right)\cdot FU'\right)$$

is greater than four; and
(g) the ratio of the number of stiff units to flexible units in said "X" segment (SU/FU) is equal to or greater than the ratio of the number of stiff units to flexible units in said "Y" segment (SU'/FU').

2. The composition of claim 1 wherein —Z— is

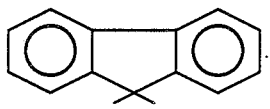

3. The composition of claim 1 wherein —Z— is

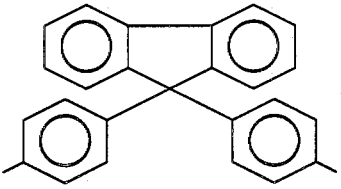

4. The composition of claim 1 wherein X has the structure:

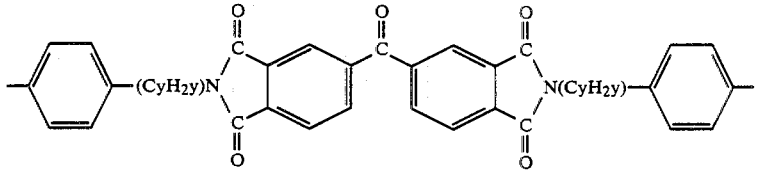

and Y has a value of from 0 to 3;
(b) "Y" represents a segment comprising stiff units (SU') and optional flexible units (FU') which stiff units and flexible units are interconnected;
(c) said stiff units, SU and SU', are independently selected from the group consisting of substituted and non-substituted aromatic rings and non-interfering heterocyclic rings;
(d) said flexible units, FU and FU', are independently selected from the group consisting of

(e) the number of "X" segments in said molecules is "a", the number of "Y" segments in said molecules is "b", and the ratio of a/(a+b) is greater than zero and less than or equal to one;
(f) the number of stiff units and flexible units is selected such that the average number of total stiff units $$\left(\left(\frac{a}{a+b}\right)\cdot SU\right)+\left(\left(\frac{b}{a+b}\right)\cdot SU'\right)$$

divided by the average number of total flexible units $$\left(\left(\frac{a}{a+b}\right)\cdot FU\right)+\left(\left(\frac{b}{a+b}\right)\cdot FU'\right)$$

5. The composition comprising linear molecules having the repeating structures:

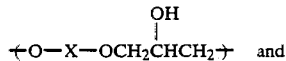   I.

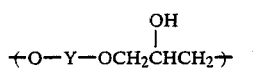   II.

wherein:
X comprises stiff units (SU) and flexible units (FU) and has the structure:

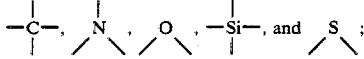

is greater than four; and (g) the ratio of the number of stiff units to flexible units in said "X" segment (SU/FU) is equal to or greater than the ratio of the number of stiff units to flexible units in said "Y" segment (SU'/FU').

6. The novel composition comprising linear molecules having the repeating structures:

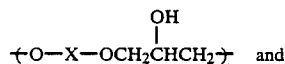 and

I.

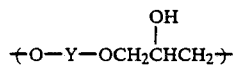

II.

wherein:
(a) "X" contains stiff units (SU) and optional flexible units (FU) which stiff and flexible units are interconnected to form a phthalocyanine radical;
(b) "Y" represents a segment comprising stiff units (SU') and optional flexible units (FU') which stiff units and flexible units are interconnected;
(c) said stiff units, SU and SU', are independently selected from the group consisting of substituted and non-substituted aromatic rings and non-interfering heterocyclic rings;
(d) said flexible units, FU and FU', are independently selected from the group consisting of

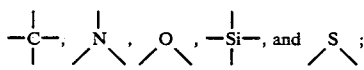

(e) the number of "X" segments in said molecules is "a", the number of "Y" segments in said molecules is "b", and the ratio of a/(a+b) is greater than zero and less than or equal to one;
(f) the number of stiff units and flexible units is selected such that the average number of total stiff units $$\left(\left(\frac{a}{a+b}\right)\cdot SU\right)+\left(\left(\frac{b}{a+b}\right)\cdot SU'\right)$$

divided by the average number of total flexible units $$\left(\left(\frac{a}{a+b}\right)\cdot FU\right)+\left(\left(\frac{b}{a+b}\right)\cdot FU'\right)$$

is greater than four; and
(g) the ratio of the number of stiff units to flexible units in said "X" segment (SU/FU) is equal to or greater than the ratio of the number of stiff units to flexible units in said "Y" segment (SU'/FU').

7. A novel composition comprising lightly crosslinked linear molecules having the repeating structures prior to crosslinking of the formula:

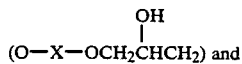 and

I.

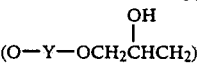

II.

where:
(a) "X" represents a segment comprising stiff units (SU) and optional flexible units (FU), which stiff units and flexible units are interconnected;
(b) "Y" represents a segment comprising stiff units (SU') and optional flexible units (FU') which stiff units and flexible units are interconnected;
(c) said stiff units, SU and SU', are independently selected from the group consisting of substituted and non-substituted aromatic rings and non-interfering heterocyclic rings;
(d) said flexible units, FU and FU', are independently selected from the group consisting of

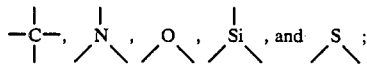

(e) the number of "X" segments in said molecules is "a", the number of "Y" segments in said molecules is "b", and the ratio of a/(a+b) is greater than zero and less than or equal to one;
(f) the number of stiff units and flexible units is selected such that the average number of total stiff units $$\left(\left(\frac{a}{a+b}\right)\cdot SU\right)+\left(\left(\frac{b}{a+b}\right)\cdot SU'\right)$$

divided by the average number of total flexible units $$\left(\left(\frac{a}{a+b}\right)\cdot FU\right)+\left(\left(\frac{b}{a+b}\right)\cdot FU'\right)$$

is greater than four; and
(g) the ratio of the number of stiff units to flexible units in said "X" segment (SU/FU) is equal to or greater than the ratio of the number of stiff units to flexible units in said "Y" segment (SU'/FU'); and
(H) wherein said repeating structures are lightly crosslinked such that between 1 and about 50 repeating structures from different molecules per 100 of said repeating structures are crosslinked together.

8. The composition of claim 7 wherein between 3 and 10 per 100 repeating structures are crosslinked together.

9. The composition of claim 7 wherein said crosslinking is obtained by addition of an effective amount of a crosslinking agent.

10. The composition of claim 9 wherein an effective amount of crosslinking agent is employed such that between about 1 and about 50 repeating structures from different molecules per 100 of said repeating structures are crosslinked together during cure.

11. The composition of claim 7 which further comprises a fibrous reinforcing material.

12. The composition of claim 10 which further comprises a fibrous reinforcing material.

13. The composition of claim 11 wherein the fibrous reinforcing material is selected from the group consisting of glass fibers, carbon fibers, boron fibers and Kevlar fibers.

14. The composition of claim 12 wherein the fibrous reinforcing material is selected from the group consisting of glass fibers, carbon fibers, boron fibers and Kevlar fibers.

15. The cured composition of claim 14 having a glass transition temperature of at least about 150° C.

16. A prepreg comprising the composition of claim 10 and a fibrous reinforcing material.

17. A prepreg comprising the composition of claim 14.

18. An article of manufacture prepared from the prepreg of claim 16.

19. The composition of claim 7 having a glass transition temperature of at least about 150° C., a flex modulus of at least 350 KSI and a fracture toughness of at least 1000 psi $\sqrt{\text{in}}$.

20. The composition of claim 9 wherein the crosslinking agent is selected from the group consisting of tri- or higher functional epoxides, tri- or higher functional phenolics, tri- or higher functional amines or mixtures thereof.

21. The composition of claim 7 wherein the average number of total stiff units divided by the average number of total flexible units is greater than 4 and less than about 20.

22. The composition of claim 21 wherein the average number of total stiff units divided by the average number of total flexible units is between about 5 and about 10.

23. The composition of claim 7 wherein the ratio of a/(a+b) is more than zero and less than 1.

24. The composition of claim 23 wherein the ratio of a/(a+b) is between about 0.4 and 0.6.

25. The composition of claim 7 wherein the ratio of

SU/FU > SU'/FU' + 0.5.

26. The composition according to claim 7 wherein the segment X has has the structure Ar—Z—Ar— where Ar is substituted or non-substituted benzene rings, optionally annulated with one or more additional benzene rings, and wherein Z represents a gem-bivalent radical having 1 to 2 aromatic hydrocarbon rings and a gem-bivalent non-aromatic ring selected from the group consisting of a ring of 5 carbon atoms, a ring of 6 carbon atoms, one of which carbon atoms may bear an oxo oxygen atom, and a ring of 5 carbon atoms and one oxygen atom, said gem-bivalent non-aromatic ring being fused to said aromatic hydrocarbon rings.

27. The composition of claim 26 wherein —Z— is

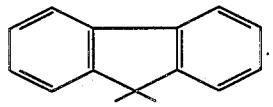

28. The composition of claim 26 wherein —Z— is

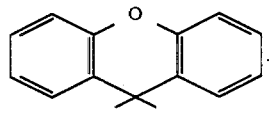

29. The composition of claim 26 wherein X has the structure:

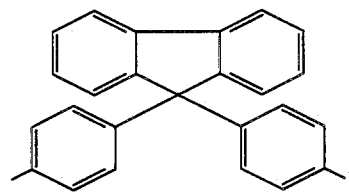

30. The composition of claim 7 wherein X has the structure

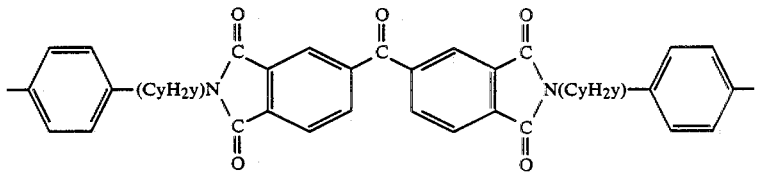

and "y" has a value of from 0 to 3.

31. The composition of claim 7 wherein X contains a phthalocyanine radical.

32. A composition according to claim 7 wherein the segment X is derived from 9,9-bis(4-hydroxyphenyl)-fluorene and the segment Y is derived from the digylcidyl ether of bis-phenol-A.

33. The process for preparing thermoplastic polymers, said process comprising reacting:
(a) a first component selected from the group consisting of phenol compounds of the formula HO—X—OH and HO—Y—OH;
(b) a second component selected from the group consisting of diepoxide compounds of the structures:

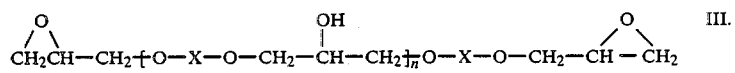

and

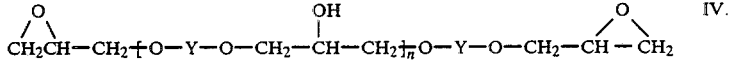

wherein n is 0 to 6 and if the phenol compound is HO—X—OH, then the diepoxide is chosen from the structure of formula III or IV and if the phenol compound is HO—Y—OH, then the diepoxide is chosen from the structure of formula III: and (c) a catalytic amount of a basic condensation catalyst at an elevated temperature and with a molar ratio of phenol compounds to diepoxides of about 0.90 to about 1.04 until the desired linear reaction product has been formed and thereafter stopping the reaction, wherein in the resulting polymer:

(i) the segment X comprises stiff units (SU) and optional flexible units (FU) and has the structure —Ar—Z—Ar— where Ar is substituted or non-substituted benzene rings, optionally annulated with one or more additional benzene rings, and wherein Z represents a gem-bivalent radical having 1 to 2 aromatic hydrocarbon rings and a gem-bivalent non-aromatic ring selected from the group consisting of a ring of 5 carbon atoms, a ring of 6 carbon atoms one of which carbon atoms may bear an oxo atom, and a ring of 5 carbon atoms and one oxygen atom, said gem-bivalent non-aromatic ring being fused to said aromatic hydrocarbon rings;

(ii) "Y" represents a segment comprising stiff units (SU') and optional flexible units (FU') which stiff units and flexible units are interconnected;

(iii) said stiff units, SU and SU', are independently selected from the group consisting of substituted and non-substituted aromatic rings, and non-interfering heterocyclic rings;

(iv) said flexible units, FU and FU', are independently selected from the group consisting of

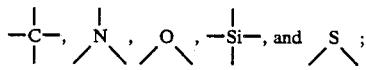

(v) the number of X segments in the resulting polymer is "a", the number of Y segments in the resulting polymer is "b", and the ratio of a/(a+b) is greater than zero and less than or equal to one;

(vi) the number of stiff units and flexible units are selected such that the average number of total stiff units in the resulting polymer $$\left(\left(\frac{a}{a+b}\right)\cdot SU\right)+\left(\left(\frac{b}{a+b}\right)\cdot SU'\right)$$

divided by the average number of total flexible units in the polymer $$\left(\left(\frac{a}{a+b}\right)\cdot FU\right)+\left(\left(\frac{b}{a+b}\right)\cdot FU'\right)$$

is greater than four; and (vii) the ratio of the number of stiff units to flexible units of said X segment (SU/FU) is equal to or greater than the ratio of the number of stiff units to flexible units in said Y segment (SU'/FU').

34. The process of claim 33 wherein —Z— is

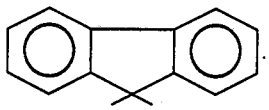

35. The process of claim 33 wherein —Z— is

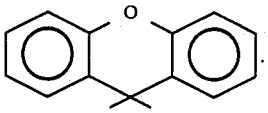

36. The process of claim 33 wherein X has the structure:

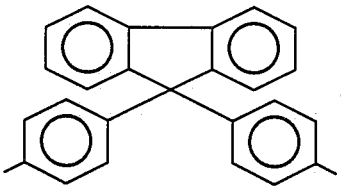

37. The process of claim 33 wherein said first component is selected from the group consisting of
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone, and
9,9-bis(4-hydroxyphenyl)phenanthrone; and
said second component is a diglycidyl ether of bisphenol-A.

38. The process of claim 33 wherein said first component is bisphenol A and said second component is selected from the group consisting of diglycidyl ethers of
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone, and
9,9-bis(4-hydroxyphenyl)phenanthrone.

39. The process of claim 33 wherein said first component is selected from the group consisting of
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone, and
9,9-bis(4-hydroxyphenyl)phenanthrone;
and said second component is selected from the group consisting of diglycidyl ethers of
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone, and
9,9-bis(4-hydroxyphenyl)phenanthrone.

40. The process of claim 37 wherein said first component is 9,9-bis(4-hydroxyphenyl)fluorene.

41. The process of claim 38 wherein said second component is the diglycidyl ether of 9,9-bis(4-hydroxyphenyl)fluorene.

42. The process of claim 39, wherein said first component is 9,9-bis(4-hydroxyphenyl)fluorene and said second component is the diglycidyl ether of 9,9-bis(4-hydroxyphenyl)fluorene.

43. The process for preparing thermoplastic polymers, said process comprising reacting:
  (a) a first component selected from the group consisting of phenol compounds of the formula HO—X—OH and HO—Y—OH;
  (b) a second component selected from the group consisting of diepoxide compounds of the structures:

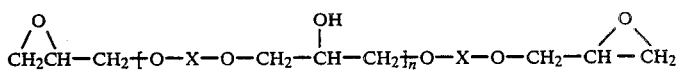 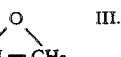

and

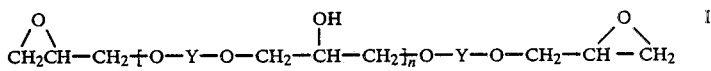 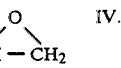

wherein n is 0 to 6 and if the phenol compound is HO—X—OH, then the diepoxide is chosen from the structure of formula III or IV and if the phenol compound is HO—Y—OH, then the diepoxide is chosen from the structure of formula III: and
  (c) a catalytic amount of a basic condensation catalyst at an elevated temperature and with a molar ratio of phenol compounds to diepoxides of about 0.90 to about 1.04 until the desired linear reaction product has been formed and thereafter stopping the reaction, wherein in the resulting polymer:
  (i) the segment X has the structure

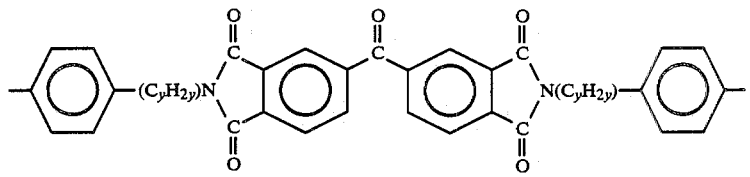

and "y" has a value of from 0 to 3;
  (ii) "Y" represents a segment comprising stiff units (SU') and optional flexible unit (FU') which stiff units and flexible units are interconnected;
  (iii) said stiff units, SU and SU', are independently selected from the group consisting of substituted and non-substituted aromatic rings, and non-interfering heterocyclic rings;
  (iv) said flexible units, FU and FU', are independently selected from the group consisting of

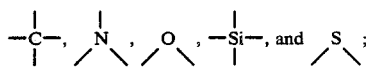

(v) the number of X segments in the resulting polymer is "a", the number of Y segments in the resulting polymer is "b", and the ratio of a/(a+b) is greater than zero and less than or equal to one;
  (vi) the number of stiff units and flexible units are selected such that the average number of total stiff units in the resulting polymer $$\left(\left(\frac{a}{a+b}\right)\cdot SU\right)+\left(\left(\frac{b}{a+b}\right)\cdot SU'\right)$$

divided by the average number of total flexible units in the polymer $$\left(\left(\frac{a}{a+b}\right)\cdot FU\right)+\left(\left(\frac{b}{a+b}\right)\cdot FU'\right)$$

is greater than four; and
  (vii) the ratio of the number of stiff units to flexible units in said X segment (SU/FU) is equal to or greater than the ratio of the number of stiff units to flexible units in said Y segment (SU'/FU').

44. A process for preparing lightly crosslinked thermoplastic polymers, said process comprising reacting a first component selected from the group consisting of phenol compounds of the formula HO—X—OH and HO—Y—OH;
  (a) a first component selected from the group consisting of phenol compounds of the formula HO—X—OH and HO—Y—OH;
  (b) a second component selected from the group consisting of diepoxide compounds of the structure:

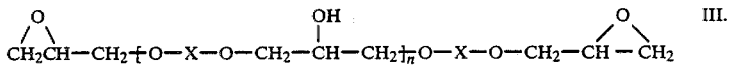 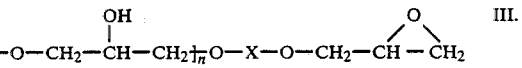

and

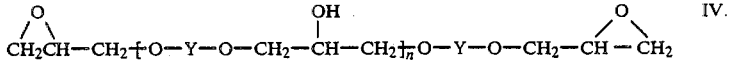

wherein n is 0 to 6 and the phenyl compound is HO—X—OH, then the diepoxide is chosen from the structure of formula III or IV and if the phenol compound is HO—Y—OH, then the diepoxide is chosen from the structure of formula III; and (c) a catalytic amount of a basic condensation catalyst at an elevated temperature and with a molar ratio of phenol compounds to diepoxides of about 0.90 to about 1.04 until the desired linear reaction product has been formed and thereafter stopping the reaction, wherein the resulting polymer is such that:

(a) "X" represents a segment comprising stiff units (SU) and optional flexible units (FU), which stiff units and flexible units are interconnected;

(b) "Y" represents a segment comprising stiff units (SU') and optional flexible units (FU') which stiff units and flexible units are interconnected;

(c) said stiff units, SU and SU', are independently selected from the group consisting of substituted and non-substituted aromatic rings and non-interfering heterocyclic rings;

(d) said flexible units, FU and FU', are independently selected from the group consisting of

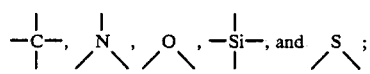

(e) the number of "X" segments in said molecules is "a", the number of "Y" segments in said molecules is "b", and the ratio of a/(a+b) is greater than zero and less than or equal to one;

(f) the number of stiff units and flexible units is selected such that the average number of total stiff units $$\left(\left(\frac{a}{a+b}\right)\cdot SU\right)+\left(\left(\frac{b}{a+b}\right)\cdot SU'\right)$$

divided by the average number of total flexible units $$\left(\left(\frac{a}{a+b}\right)\cdot FU\right)+\left(\left(\frac{b}{a+b}\right)\cdot FU'\right)$$

is greater than four; and (g) the ratio of the number of stiff units to flexible units in said segment "X" (SU/FU) is equal to or greater than the ratio of the number of stiff units to flexible units in said "Y" segment (SU'/FU'); and (h) lightly crosslinking the polymer such that between 1 and about 50 repeating structures from different molecules per 100 of said repeating structures of the polymer are crosslinked together during cure.

45. The process according to claim 44 wherein said crosslinking is obtained by addition of an effective amount of a crosslinking agent.

46. The process of claim 45 wherein the crosslinking agent is selected from the group consisting of tri- or higher functional epoxides, tri- or higher functional phenolics, tri- or higher functional amines or mixtures thereof.

47. The process of claim 44 wherein the amount of catalyst employed is not in excess of 0.1 mole per mole of said first component.

48. The process of claim 44 wherein said first and second components are reacted at a temperature of about 130° C. to about 230° C. for about 1 to about 24 hours.

49. The process of claim 44 wherein the average number of total stiff units divided by the average number of total flexible units is greater than 4 and less than about 20.

50. The process of claim 49 wherein the average number of total stiff units divided by the average number of total flexible units is between about 5 and about 10.

51. The process of claim 44 wherein the ratio of a/(a+b) is more than zero and less than 1.

52. The composition of claim 51 wherein the ratio of a/(a+b) is between about 0.4 and 0.6.

53. The process of claim 44 wherein the ratio of

SU/FU > SU'/FU' + 0.5.

54. The process according to claim 44 wherein the segment X has the structure —Ar—Z—Ar— where Ar is substituted or non-substituted benzene rings, optionally annulated with one or more additional benzene rings, and wherein Z represents a gem-bivalent radical having 1 to 2 aromatic hydrocarbon rings and a gem-valent non-aromatic ring selected from the group consisting of a ring of 5 carbon atoms, a ring of 6 carbon atoms, one of which carbon atoms may bear an oxo oxygen atom, and a ring of 5 carbon atoms and one oxygen atom, said gem-bivalent non-aromatic ring being fused to said aromatic hydrocarbon rings.

55. The process of claim 54 wherein —Z— is

56. The process of claim 54 wherein —Z— is

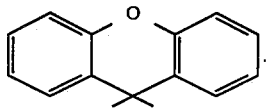

57. The composition of claim 54 wherein X has the structure:

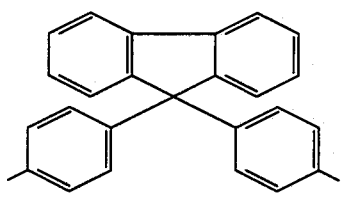

58. The process of claim 44 wherein X has the structure

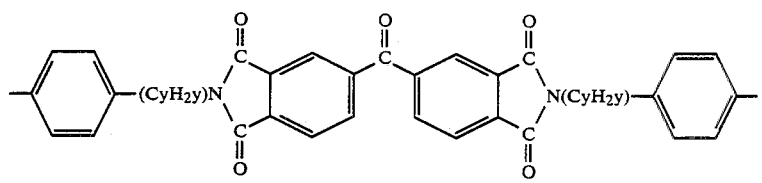
and "y" has a value of from 0 to 3.
59. A process according to claim 44 wherein the first component is the diglycidyl ether of bis-phenol-A and the second component is 9.9-bis(4-hydroxyphenyl)fluorene.
* * * * *

UNITED STATES PATENT AND TRADEMARK OFFICE
CERTIFICATE OF CORRECTION

PATENT NO. : 4,786,668
DATED : November 22, 1988
INVENTOR(S) : Kenneth C. Dewhirst It is certified that error appears in the above-identified patent and that said Letters Patent is hereby corrected as shown below:

Claim 1, line 8, cancel "-A-Z-Ar-" and insert -- -Ar-Z-Ar- --.

Signed and Sealed this

Sixteenth Day of May, 1989

Attest:

DONALD J. QUIGG

*Attesting Officer*   *Commissioner of Patents and Trademarks*